US009017289B2

(12) United States Patent  
Backes

(10) Patent No.: US 9,017,289 B2  
(45) Date of Patent: Apr. 28, 2015

(54) TRANSDERMAL FLUID DELIVERY DEVICE

(75) Inventor: Larry P. Backes, Guilford, CT (US)

(73) Assignee: Covidien LP, Mansfield, MA (US)

( * ) Notice: Subject to any disclaimer, the term of this patent is extended or adjusted under 35 U.S.C. 154(b) by 532 days.

(21) Appl. No.: 13/275,659

(22) Filed: Oct. 18, 2011

(65) Prior Publication Data

US 2012/0109065 A1 May 3, 2012

Related U.S. Application Data

(60) Provisional application No. 61/409,690, filed on Nov. 3, 2010.

(51) Int. Cl.
*A61M 5/00* (2006.01)
*A61M 25/00* (2006.01)
*A61M 5/32* (2006.01)
*A61M 37/00* (2006.01)

(52) U.S. Cl.
CPC ... *A61M 37/0015* (2013.01); *A61M 2037/0023* (2013.01); *A61M 2037/003* (2013.01); *A61M 2037/0061* (2013.01)

(58) Field of Classification Search
CPC ............. A61M 2037/0023; A61M 2037/003; A61M 2037/0061; A61M 37/0015; A61M 5/178; A61M 35/003; A61M 5/158; A61M 3/0279; A61M 2037/0046; A61M 25/0084; A61M 5/3287; A61M 5/3295; A61M 5/32; A61M 5/14244; A61M 5/14248; A61M 5/3298; A61K 9/0021; A61B 17/205; A61B 5/685
USPC ............. 604/173, 19, 21, 264, 207–209, 272, 604/181, 187; 606/167
See application file for complete search history.

(56) References Cited

U.S. PATENT DOCUMENTS

| | | |
|---|---|---|
| 5,997,501 A | 12/1999 | Gross et al. |
| 6,083,196 A | 7/2000 | Trautman et al. |
| 6,537,242 B1 | 3/2003 | Palmer |
| 6,562,014 B2 | 5/2003 | Lin et al. |
| 6,611,707 B1 | 8/2003 | Prausnitz et al. |
| 6,656,147 B1 | 12/2003 | Gertsek et al. |
| 6,689,103 B1 * | 2/2004 | Palasis .................. 604/173 |
| 6,743,211 B1 | 6/2004 | Prausnitz et al. |
| 6,767,341 B2 | 7/2004 | Cho |
| 6,780,171 B2 | 8/2004 | Gabel et al. |
| 6,896,666 B2 | 5/2005 | Kochamba |
| 7,004,928 B2 | 2/2006 | Aceti et al. |
| 7,047,070 B2 | 5/2006 | Wilkinson et al. |
| 7,066,922 B2 | 6/2006 | Angel et al. |
| 7,097,631 B2 * | 8/2006 | Trautman et al. ........... 604/46 |

(Continued)

*Primary Examiner* — Bhisma Mehta  
*Assistant Examiner* — Bradley G Thomas, Jr.

(57) ABSTRACT

A transdermal fluid delivery device includes a housing defining a longitudinal axis and having a proximal end and a distal end. The housing defines a passageway extending longitudinally therethrough. A fluid reservoir is disposed at the proximal end of the housing in communication with the passageway of the housing and is adapted for retaining a fluid therein. A base member is positioned at the distal end of the housing. A microneedle assembly including a plurality of microneedles extending distally therefrom is also provided. The microneedle assembly is selectively moveable with respect to the housing between a retracted position, wherein the microneedles are disposed within the housing, and an extended position, wherein the microneedles are advanced distally to penetrate the base member and extend distally therefrom for puncturing the patient's epidermis and delivering the fluid into the patient's bloodstream.

9 Claims, 2 Drawing Sheets

(56) References Cited

U.S. PATENT DOCUMENTS

| | | |
|---|---|---|
| 7,156,838 B2 | 1/2007 | Gabel et al. |
| 7,166,086 B2 * | 1/2007 | Haider et al. .................. 604/46 |
| 7,226,439 B2 | 6/2007 | Prausnitz et al. |
| 7,364,568 B2 | 4/2008 | Angel et al. |
| 7,375,139 B2 | 5/2008 | Aldred |
| 7,429,258 B2 | 9/2008 | Angel et al. |
| 2004/0092875 A1 | 5/2004 | Kochamba |
| 2004/0162521 A1 * | 8/2004 | Bengtsson .................. 604/136 |
| 2005/0027242 A1 | 2/2005 | Gabel et al. |
| 2005/0165380 A1 | 7/2005 | Kochamba |
| 2006/0264926 A1 | 11/2006 | Kochamba |
| 2007/0010810 A1 | 1/2007 | Kochamba |
| 2007/0038181 A1 * | 2/2007 | Melamud et al. ............. 604/158 |
| 2007/0088348 A1 | 4/2007 | Kochamba |
| 2007/0260201 A1 | 11/2007 | Prausnitz et al. |
| 2008/0200863 A1 | 8/2008 | Chomas et al. |
| 2009/0118662 A1 * | 5/2009 | Schnall .......................... 604/20 |
| 2011/0276027 A1 * | 11/2011 | Trautman et al. ............ 604/506 |

\* cited by examiner

TRANSDERMAL FLUID DELIVERY DEVICE

CROSS-REFERENCE TO RELATED APPLICATION

This application claims the benefit of and priority to U.S. Provisional Patent Application No. 61/409,690, filed on Nov. 3, 2010, the entire contents of which are hereby incorporated by reference herein.

BACKGROUND

1. Technical Field

The present disclosure relates generally to devices for transdermal fluid delivery of medicaments. More particularly, the present disclosure relates to micro-needle array patches for transdermal fluid delivery of drugs and/or nutrients.

2. Background of the Related Art

Transdermal fluid delivery of drugs is an effective and convenient way for patients to receive medications and/or nutrients. Transdermal fluid delivery of drugs is particularly useful where a patient needs to maintain a continuous level of medication in the blood stream over an extended period of time, where the patient is likely to forget to take medication or has difficulty taking medication orally, and/or where the patient is unable to properly absorb the medications or nutrients through the digestive system. However, not all drugs and nutrients are easily absorbed through the epidermis. For example, the molecules of the drugs or nutrients may be too large, the drugs or nutrients may be too lipophobic, and/or the required dose may be too large to be efficiently absorbed by the epidermis.

More recently, transdermal patches including microneedle arrays have been used to puncture the epidermal layer to deliver drugs and/or nutrients into the blood stream, circumventing some of the limitations associated with absorbing the drugs and/or nutrients through the epidermis. However, when these micro-needle arrays are removed from the patient's epidermis, the punctures created by the needles, if not properly protected, provide a potential avenue for the introduction of virus and bacteria into the blood stream. Additionally, if the needles are not properly maintained prior to insertion, virus and/or bacteria on the needles themselves may infect the patient upon insertion of the micro-needle array.

For example, U.S. Pat. No. 7,226,439 discloses a microneedle drug delivery device including a reservoir and a substrate having one or more microneedles attached thereto and extending therefrom. The reservoir is selectably connectable to the substrate such that the reservoir contents can flow from the reservoir out through the tips of the microneedles. In use, the microneedles are inserted into the skin, while the substrate is retained in position on the skin by an adhesive. The reservoir may then be connected to the substrate for delivering the drugs to the patient. At the completion of treatment, the substrate is removed from the patient's skin, leaving behind a plurality of open puncture wounds where the microneedles were inserted. These unprotected, open puncture wounds are susceptible to disease and/or infection. Further, there is the risk that the exposed microneedles may become contaminated prior to insertion into the patient's skin, putting the patient at risk of disease and/or infection.

SUMMARY

In accordance with the present disclosure, a transdermal fluid delivery device is provided. The transdermal fluid delivery device is positionable on a patient's epidermis for delivering fluid into the patient's bloodstream. The transdermal fluid delivery device includes a housing defining a longitudinal axis and having a proximal end and a distal end. The housing defines a passageway extending longitudinally therethrough. A fluid reservoir is disposed at the proximal end of the housing in communication with the passageway. The fluid reservoir is adapted to retain a fluid, e.g., drugs and/or nutrients, therein. A base member is positioned at the distal end of the housing. A microneedle assembly including a plurality of microneedles extending distally therefrom is initially disposed within the housing. The microneedle assembly is selectively moveable with respect to the housing between a retracted position, wherein the microneedles are disposed within the housing, and an extended position, wherein the microneedles are advanced distally to penetrate the base member and extend distally therefrom. In the extended position, the microneedles are adapted for puncturing the patient's epidermis to deliver fluid into the patient's bloodstream.

In one embodiment, at least a portion of the housing is rotatable with respect to the microneedle assembly about the longitudinal axis of the housing between a first position and a second position for moving the microneedle assembly between the retracted position and the extended position. More specifically, a helical cam surface may be formed on an inner surface of the portion of the housing and the microneedle assembly may include one (or more) protrusions engaged with the cam surface such that, upon rotation of the portion of the housing with respect to the microneedle assembly, the protrusions travel along the helical cam surface, translating the microneedle assembly longitudinally with respect to the housing.

In another embodiment, a latching mechanism may be included for retaining the microneedle assembly in the retracted position and/or the extended position. Further, the microneedle assembly may be biased towards the retracted position or the extended position.

In yet another embodiment, the microneedle assembly is longitudinally translatable with respect to the housing between a first position and a second position for moving the microneedle assembly between the retracted position and the extended position.

In still another embodiment, the microneedle assembly includes a first latch member and the housing includes a second, complementary latch member such that, upon movement of the microneedle assembly to the extended position, the first and second latch members engage one another to retain the microneedle assembly in the extended position.

In still yet another embodiment, one (or both) of the first and second latch members defines a pre-determined latching period. Accordingly, the latch member may be configured to disengage the other latch member at the end of the pre-determined latching period such that the microneedle assembly is permitted to return to the retracted position.

In yet another embodiment, a skin adhesive is disposed on a distal surface of the base member for adhering the housing to the patient's epidermis. A peelable cover may be disposed over the skin adhesive to preserve the skin adhesive and to inhibit adhesion prior to use.

In still another embodiment, when the microneedle assembly is moved to the extended position, the microneedles are configured to extend distally from the base member by about 2 mm to about 3 mm. Further, the microneedles may include pointed distal ends to facilitate penetrating the base member and/or puncturing the patient's epidermis.

Another embodiment of a transdermal fluid delivery device provided in accordance with the present disclosure includes a housing, a fluid reservoir, a base member, and a microneedle assembly. The housing defines a longitudinal axis and includes a proximal end and a distal end. The housing also defines a passageway extending longitudinally therethrough and a helical cam track formed on an inner surface thereof. The housing is rotatable between a first position and a second position. The fluid reservoir positionable within the passageway of the housing and is adapted to retain a fluid therein. The base member is positioned at the distal end of the housing. The microneedle assembly is coupled to the fluid reservoir and includes a plurality of microneedles extending distally therefrom. The microneedle assembly including at least one protrusion extending therefrom that is configured to engage the cam track of the housing such that, upon rotation of the housing between the first and second positions, the microneedle assembly is translated longitudinally relative to the housing between a retracted position, wherein the microneedles are disposed within the base member, and an extended position, wherein the microneedles extend distally from the base member for puncturing the patient's epidermis and delivering the fluid into the patient's bloodstream. The transdermal fluid delivery device may further be configured similarly to any of the embodiments above.

Another embodiment of a transdermal fluid delivery device provided in accordance with the present disclosure includes a housing, a fluid reservoir, a base member, and a microneedle assembly. The housing defines a longitudinal axis and includes a proximal end, a distal end, and a passageway extending longitudinally therethrough. The fluid reservoir is positionable within the passageway of the housing and is adapted to retain a fluid therein. The base member is positioned at the distal end of the housing. The microneedle assembly is coupled to the fluid reservoir and includes a plurality of microneedles extending distally therefrom. The microneedle assembly is longitudinally translatable with respect to the housing between a retracted position, wherein the microneedles are disposed within the base member, and an extended position, wherein the microneedles extend distally from the base member for puncturing the patient's epidermis and delivering the fluid into the patient's bloodstream. The transdermal fluid delivery device may further be configured similarly to any of the embodiments above.

BRIEF DESCRIPTION OF THE DRAWINGS

Various exemplary embodiments of the present disclosure are described herein below with reference to the drawings, wherein.

DETAILED DESCRIPTION OF THE EMBODIMENTS

Figure 1:
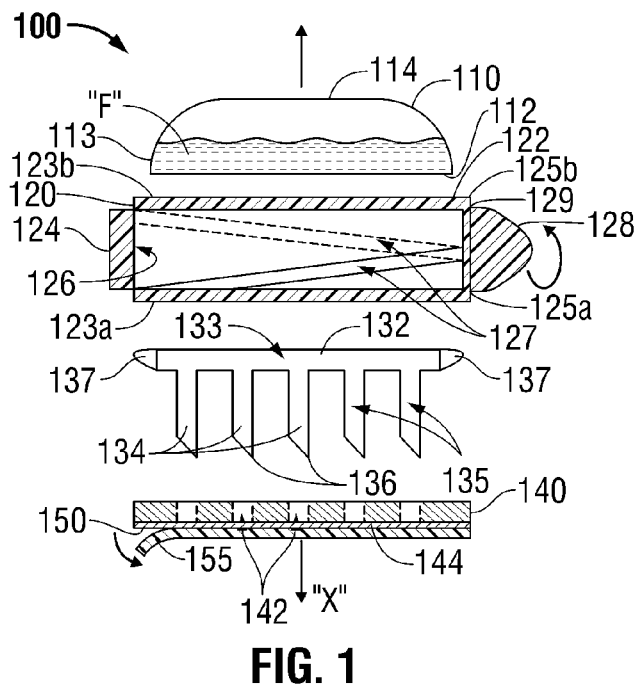
FIG. 1 is a side, cross-sectional view of one embodiment of a transdermal fluid delivery device in accordance with the present disclosure, shown with parts separated.

Various embodiments of the present disclosure and methods of using the same will now be described in detail with reference to the drawings wherein like references numerals identify similar or identical elements. In the drawings, and in the following description, the term "proximal" should be understood as referring to the end of the device, or component thereof, that is closer to the clinician during proper use, while the term "distal" should be understood as referring to the end that is farther from the clinician, as is traditional and conventional in the art.

Referring now to FIG. 1, one embodiment of a transdermal fluid delivery device in accordance with the present disclosure is show identified by reference numeral 100. Transdermal fluid delivery device 100 generally includes a fluid reservoir 110, a housing 120, a microneedle assembly 130, and a base 140. Fluid reservoir 110 is engaged to microneedle assembly 130 and, upon actuation, is in fluid communication with microneedle assembly 130 such that fluid "F" from fluid reservoir 110 may flow through microneedle assembly 130 for transdermal fluid delivery of the fluid "F" to a patient. Housing 120 includes a frame 122 and a rotatable collar 124. Housing 120 is disposed about fluid reservoir 110 and microneedle assembly 130 and defines a longitudinal axis "X." Base 140 is engaged to frame 122 of housing 120 at a distal end 123a thereof and is configured for positioning on a patients skin to retain transdermal fluid delivery device 100 thereon. As will be described in greater detail below, microneedle assembly 130 is axially translatable, upon rotation of collar 124 of housing 120, between an initial, retracted position (FIG. 2), wherein microneedle assembly 130 is fully disposed within rotatable collar 124, and an extended position (FIG. 3), wherein microneedle assembly 130 extends at least partially from rotatable collar 124 and through base 140 in a distal direction, e.g., to penetrate the patient's skin.

Fluid reservoir 110 is adapted to retain a fluid "F," e.g., medicaments, nutrients, or other treatment fluids, therein for delivery to the patient. Fluid reservoir 110 is disposed at a proximal end of microneedle assembly 130 and is sealingly engaged thereto. More specifically, fluid reservoir 110 includes a rigid, or semi-rigid seal ring 112 disposed at a distal end 113 thereof for sealingly engaging hub 132 of microneedle assembly 130. Further, a penetrable membrane or other barrier (not shown) may be disposed between fluid reservoir 110 and hub 132 of microneedle assembly 130 to inhibit fluid "F" from passing distally from fluid reservoir 110 into microneedle assembly 130 prior to actuation. The penetrable membrane (not shown) may be penetrated to permit the passage of fluid "F" therethrough upon moving microneedle assembly 130 from the retracted position (FIG. 2) to the extended position (FIG. 3), e.g., via the rotation of collar 124, or, in embodiments where fluid reservoir 110 is elastomeric, upon depression of fluid reservoir 110. Alternatively, any other suitable mechanism may be provided for penetrating the penetrable membrane (not shown). It is also envisioned that a selectively controlled barrier (not shown) may be provided, allowing the user to selectively permit/inhibit the flow of fluid "F" from fluid reservoir 110 into hub 132 of microneedle assembly 130.

With continued reference to FIG. 1, fluid reservoir 110 may define a dome-like configuration wherein seal ring 112 is disposed at distal end 113 of fluid reservoir 110 and defines the base portion of fluid reservoir 110 and wherein proximal end 114 of fluid reservoir 110 defines the apex portion of the dome-shaped reservoir 110. Further, fluid reservoir 110 may be formed from any suitable bio-compatible material, e.g., polymeric materials or, more specifically, elastomeric materials. It is also envisioned that fluid reservoir 110 be non-porous, to inhibit gas from penetrating therethrough or loss of fluid "F." Such a feature is particularly useful where the drugs or nutrients contained within fluid reservoir 110 are sensitive to oxygen, for example, or other gases. In embodiments where fluid reservoir 110 is formed from an elastomeric material, fluid reservoir 110 may be biased toward a collapsed state, such that the "F" fluid within fluid reservoir 110 is urged, or biased distally toward microneedle assembly 130 to facilitate delivery of the fluid "F" into microneedle assembly 130 and, eventually, to the patient. Such a configuration is particularly useful where the drugs and/or nutrients to be delivered are more viscous, or where the fluid "F" contains suspended particles therein. In either configuration, it is envisioned that fluid reservoir 110 be capable of withstanding rubbing, bumping, brushing, and/or other typical external forces acting on fluid reservoir 110, such that the fluid reservoir 110 does not puncture or rupture during use. The particular size, volume and configuration of fluid reservoir 110 may be determined, for example, by the amount of fluid to be delivered, the time frame for delivery, and/or the specific properties of the fluid to be delivered.

As mentioned above, housing 120 includes a frame 122 and a rotatable collar 124. Frame 122 defines an annular, or ring-like configuration including a proximal end 123b, a distal end 123a and a passageway, or lumen extending therethrough. Rotatable collar 124 is positioned within frame 122 and similarly defines an annular, or ring-like configuration including a proximal end 125b, a distal end 125a and a passageway, or lumen extending therethrough. Housing 120 may be formed from any suitable bio-compatible material, e.g., polymeric materials. An inner surface 126 of rotatable collar 124, which defines the lumen extending therethrough, may include a helical ramp, or cam track 127 defined therein. Helical cam track 127 is positioned about longitudinal axis "X" and defines a pre-determined pitch, or slope. As will be described in greater detail below, cam track 127 is configured to retain hub 132 of microneedle assembly 130 therein such that, upon rotation of rotatable collar 124 about longitudinal axis "X," hub 132 of microneedle assembly 130 is moved, or cammed along cam track 127, translating microneedle assembly 130 longitudinally with respect to housing 120 according to the pre-determined pitch of helical cam track 127. Rotatable collar 124 may further include a flange 128 positioned on an outer circumferential surface 129 thereof and extending radially outwardly therefrom through a slot (not explicitly shown) defined within frame 122 of housing 120 to facilitate rotation of collar 124 with respect to microneedle assembly 130 and/or to provide a visual indication as to the relative positioning of collar 124 with respect to microneedle assembly 130.

As shown in FIG. 1, microneedle assembly 130 includes a proximal hub 132 having a plurality of microneedles 134 extending distally therefrom. Hub 132 includes a pair of protrusions 137 extending radially outwardly therefrom at opposite sides thereof. Protrusions 137 are engaged within cam track 127 defined within inner surface 126 of collar 124 to facilitate longitudinal translation of microneedle assembly 130 with respect to collar 120 upon rotation of collar 124 about longitudinal axis "X." In other words, protrusions 137 of hub 132 engage cam track 127 such that hub 132 is movable along cam track 127 upon rotation of collar 124.

Each microneedle 134 of microneedle assembly 130 includes a lumen 135 extending therethrough. Hub 132 includes an open proximal end 133 in communication with each of lumens 135 of microneedles 134 such that the fluid "F" disposed within fluid reservoir 110 may flow into hub 132, via open proximal end 133 thereof, and into lumens 135 of microneedles 134. Each microneedle 134 may define an angled, or beveled distal end 136 configured to facilitate passage of fluid therethrough, to facilitate penetrating base 140 and/or to facilitate puncturing of the patient's epidermis, although other configurations are contemplated. As can be appreciated, the number, configuration and dimensions of microneedles 134 may depend, at least in part, on the viscosity of the fluid to be delivered, the volume of fluid to be delivered, the chemical properties of the fluid to be delivered, and/or the desired delivery rate, or flow rate of the fluid into the patient's bloodstream.

Base 140 of transdermal fluid delivery device 100 is adapted to engage frame 122 of housing 120 at distal end 123a of frame 122. Base 140 may define a relatively thin membrane, e.g., a non-porous elastomeric membrane, or may define a more substantial foundation, e.g., a polymeric foundation, that includes a membrane disposed about a distal surface thereof. In either embodiment, it is envisioned that base 140 is configured to fixedly engage distal end 123a of frame 122 of housing 120, while also being penetrable by microneedles 134 of microneedle assembly 130. Further, it is contemplated that base 140 be somewhat rigid to provide structural support to transdermal fluid delivery device 100, but also be somewhat flexible to conform to the contours of the patient, to effect an efficient adhesion therebetween. In embodiments where base 140 defines a foundation, base 140 may include a plurality of perforated microneedle channels 142 defined therein corresponding to microneedles 134 of microneedle assembly 130 to facilitate the penetration of microneedles 134 through base 140.

With continued reference to FIG. 1, an adhesive or, more particularly, a skin adhesive 150, may be disposed on a distal surface 144 of base 140 of transdermal fluid delivery device 100 for adhering transdermal fluid delivery device 100 to a patient's epidermis, or skin, e.g., on a patient's arm. As such, skin adhesive 150, e.g., a silicon adhesive, must have sufficient strength to retain transdermal fluid delivery device 100 on the patient's arm and must be capable of withstanding rubbing from clothing, inadvertent bumping or brushing, movement of the arm, and/or other typical activity by the patient. Skin adhesive 150 must also be sufficiently strong to inhibit dislodging or repositioning of fluid delivery device 100 upon rotation of collar 124. However, on the other hand, skin adhesive 150 must also permit removal of transdermal fluid delivery device 100 from the patient's skin with minimal trauma and/or pain to the patient when treatment is complete.

A peelable cover, or backing 155 may also be provided for maintaining the integrity of adhesive 150, for protecting transdermal fluid delivery device 100, e.g., for preventing contaminants from adhering to transdermal fluid delivery device 100, and/or for inhibiting inadvertent adhesion of transdermal fluid delivery device 100 prior to use or prior to proper positioning. As shown in FIG. 1, cover 155 may initially be disposed over adhesive 150 and may be peeled off or otherwise removed and discarded prior to the use of transdermal fluid delivery device 100, e.g., prior to adhesion to the patient's skin.

Figure 2:
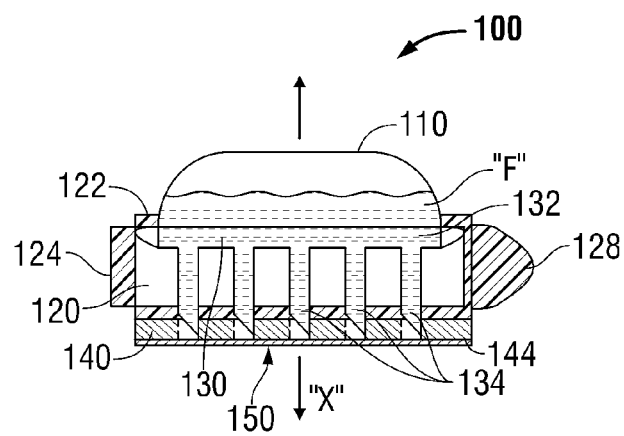
FIG. 2 is a side, cross-sectional view of the transdermal fluid delivery device of FIG. 1 shown disposed in a retracted position.
Figure 3:
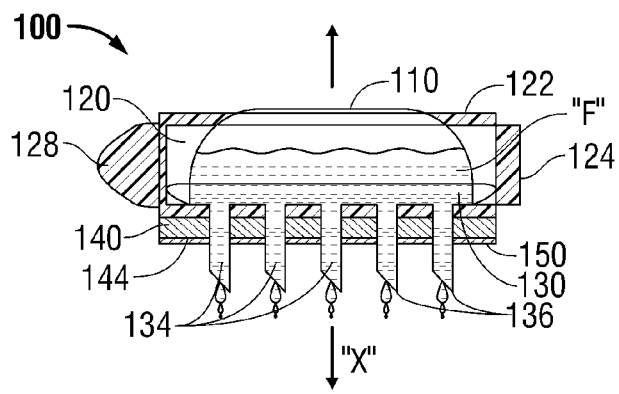
FIG. 3 is a side, cross-sectional view of the transdermal fluid delivery device of FIG. 1 shown disposed in an extended position.

Turning now to FIGS. 2 and 3, the use and operation of transdermal fluid delivery device 100 will be described.

Transdermal fluid delivery device 100 may come pre-assembled, e.g., wherein fluid reservoir 110 is pre-filled with the drugs and/or nutrients to be delivered and is engaged, or integrally formed with hub 132 of microneedle assembly 134. In such an embodiment, transdermal fluid delivery device 100 may be configured as a disposable device wherein the internal components of transdermal fluid delivery device 100 are pre-sterilized. Accordingly, the user need only remove transdermal fluid delivery device 100 from its packaging (not shown), remove peelable cover 155, and adhere transdermal fluid delivery device 100 to the patient's epidermis, e.g., to the patients upper arm. Since the fluid, e.g., the drugs and/or nutrients, as well as the microneedle assembly 130 are sealed within transdermal fluid delivery device 100, via base 140, the risk of contaminants, e.g., bacteria, entering fluid reservoir 110 and/or contaminating the microneedle assembly 130 prior to, during, or after use, is substantially reduced. Thus, the risk of infection to the patient is substantially reduced. Alternatively, transdermal fluid delivery device 100 may be configured, at least partially, as a sterilizable, reusable device 100.

Initially, the surface of the patient's skin is cleaned and sterilized in accordance with known techniques. Next, in preparation for use, peelable cover 155 is removed such that skin adhesive 150 is exposed. Lead by distal surface 144 of base 140 having the exposed skin adhesive 150 thereon, transdermal fluid delivery device 100 is urged into contact with the patient's epidermis to securely adhere transdermal fluid delivery device 100 thereto. At this point, as shown in FIG. 2, microneedle assembly 130 is disposed in the initial, or retracted position within housing 120, as indicated by the position flange 128 of rotatable collar 124 extending from housing 120, and the fluid "F" is retained within fluid reservoir 110 by the penetrable membrane (not shown). In this retracted position, as discussed above, microneedles 134 are fully disposed within housing 120, e.g., microneedles 134 do not extend from base 140. This configuration, wherein transdermal fluid delivery device 100 is disposed on the patient's skin prior to deployment of the microneedles 134 inhibits contamination of microneedles 134 prior to deployment through the patient's epidermis. In other words, the likelihood of contamination of microneedles 134 by the external environment is greatly reduced since, as will be described below, microneedles 134 are deployed from housing 120 directly into the patient's epidermis, with little or no contact with the external environment. Similarly, since transdermal fluid delivery device 100 is adhered to the epidermis prior to any puncture wounds being created for insertion of microneedles 134, the likelihood of bacteria, disease, or contaminants entering the patient's blood stream is greatly reduced.

In order to begin treatment, e.g., to deliver fluid, drugs and/or nutrients transdermally into the patient's bloodstream, the user grasps flange 128 of rotatable collar 124 to rotate collar 124 about longitudinal axis "X" and with respect to microneedle assembly 130 from the position shown in FIG. 2, to the position shown in FIG. 3, e.g., collar 124 is rotated 180 degrees with respect to microneedle assembly 130 in the clockwise direction (although it is envisioned that collar 124 may alternatively be configured to rotate counterclockwise from the initial position or through other degrees of rotation (i.e., greater or less than 180 degrees). Accordingly, as collar 124 is rotated with respect to microneedle assembly 130, protrusions 137 of hub 132 of microneedle assembly 130 are cammed, or ramped along cam track 127 of collar 124. As mentioned above, the pitch, or slope of cam track 127 causes hub 132 to be translated distally along longitudinal axis "X" and with respect to housing 120 upon clockwise rotation of collar 124. Upon rotation of collar 124 to move microneedle assembly 130 to the extended position, the penetrable membrane (not shown) is penetrated, allowing fluid "F" to flow into hub 132 of microneedle assembly 130. Alternatively, the penetrable membrane or other selectively controlled barrier (not shown) may be penetrated or opened once the microneedle assembly 130 is moved to the extended position.

Distal translation of hub 132 of microneedle assembly 130 causes microneedles 134 to move toward the extended position. When moved to the extended position, microneedles 134 penetrate through base 140, e.g., through perforated microneedle channels 142, and through the patient's epidermis. As mentioned above, the configuration of microneedles 134 facilitates penetration of microneedles 134 through base 140 and through the epidermis. It is envisioned that transdermal fluid delivery device 100 be configured such that, in the extended position, microneedles 134 extend a sufficient distance from base 140 to fully penetrate the epidermis, e.g., by about 2 mm-3 mm. Further, housing 120 may include a locking feature (not shown) for fixing the position of collar 124, e.g., such that microneedle assembly 130 may be fixed, or locked in the extended position (and/or the retracted position). Additionally, microneedle assembly 130 may be biased toward the retracted position or the extended position.

As can be appreciated, and as shown in FIG. 3, with microneedles 134 disposed through the patient's epidermis, the fluid "F" within fluid reservoir 110 is permitted to flow from fluid reservoir 110, through hub 132 of microneedle assembly 130, through lumens 135 of microneedles 134 and out distal tips 136 of microneedles 134 into the patient's bloodstream. Transdermal fluid delivery device 100 is left adhered to the skin, or epidermis, with microneedles 134 penetrating therethrough until the desired amount of fluid "F" has been delivered to the patient. The specific amount of delivery time may depend on the configuration of transdermal fluid delivery device 100, the fluids "F" to be delivered to the patient, and/or the specific treatment program being followed. Further, transdermal fluid delivery device 100 may be configured for continuous delivery of fluids "F," or may be configured for intermittent delivery of fluids "F," e.g., upon depression of fluid reservoir 110.

In any configuration, once treatment is complete, collar 124 is rotated back from the extended position, shown in FIG. 3, to the initial position, e.g., collar 124 is rotated 180 degrees in a counterclockwise direction about longitudinal axis "X," shown in FIG. 2. As collar 124 is rotated, hub 132 of microneedle assembly 130 is ramped, or cammed along cam track 127, translating microneedle assembly 130 proximally along longitudinal axis "X" and with respect to housing 120. As microneedle assembly 130 is translated proximally, microneedles 134 are retracted from the patient's epidermis and back through base 140 to the retracted position, wherein microneedles 134 are disposed within housing 120.

With microneedle assembly 130 returned to the retracted position within housing 120, transdermal fluid delivery device 100 remains affixed to the patient's skin. More specifically, transdermal fluid delivery device 100, which remains adhered to the patient's skin, covers the puncture wounds created by microneedles 134. As can be appreciated, allowing microneedles 134 to be retracted, or removed from the skin, without exposing the puncture wounds left behind to contamination from the external environment helps prevent infection and disease. Thus, the puncture wounds may be permitted to heal prior to removal of transdermal fluid delivery device 100 from the skin. Once the wounds have healed, or once the likelihood of infection, disease, or bacteria entering the body through the puncture wounds is reduced to an acceptable level, transdermal fluid delivery device 100 may be removed and discarded (or sterilized for repeated use).

Figure 4:
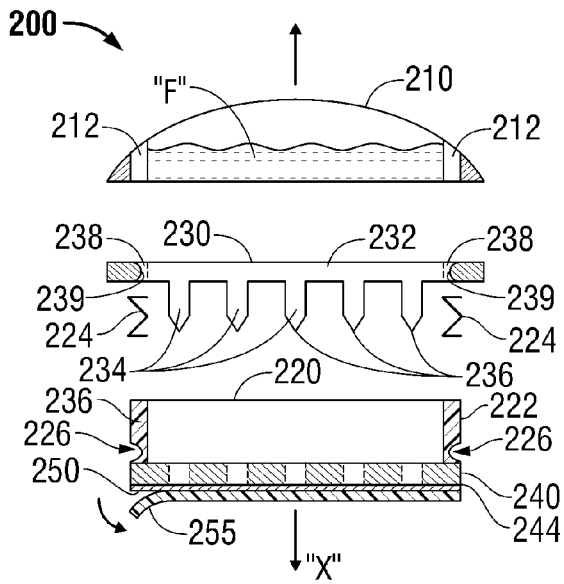
FIG. 4 is a side, cross-sectional view of another embodiment of an transdermal fluid delivery device in accordance with the present disclosure, shown with parts separated.
Figure 5:
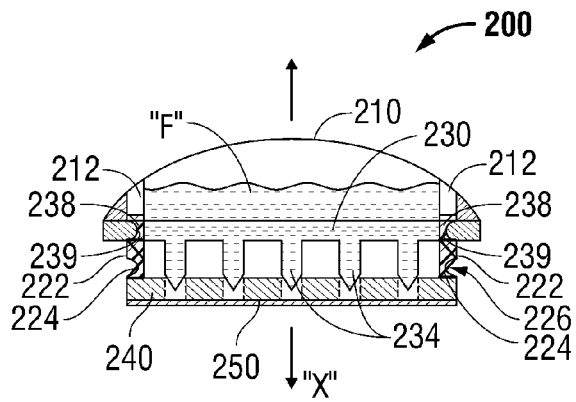
FIG. 5 is a side, cross-sectional view of the transdermal fluid delivery device of FIG. 4 shown disposed in the retracted position.
Figure 6:
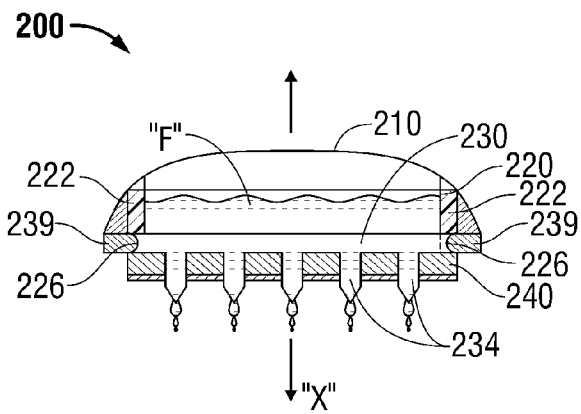
FIG. 6 is a side, cross-sectional view of the transdermal fluid delivery device of FIG. 4 shown disposed in the extended position.

Turning now to FIGS. 4-6, another embodiment of a transdermal fluid delivery device is shown identified by reference numeral 200. Transdermal fluid delivery device 200 is similar to transdermal fluid delivery device 100 (FIG. 1) and generally includes a fluid reservoir 210, a housing 220, a microneedle assembly 230, and a base 240. Fluid reservoir 210 is adapted to retain a fluid "F," e.g., medicaments, nutrients, or other treatment fluids, therein for delivery to the patient and may be configured similarly to fluid reservoir 110 (FIG. 1), discussed above. Further, fluid reservoir 210 is sealingly engaged to microneedle assembly 230 and includes a pair of guide channels 212 disposed on opposing sides thereof. As in the previous embodiment, a penetrable membrane or selectively controlled barrier (not shown) may be disposed between fluid reservoir 210 and microneedle assembly 230, to inhibit the passage of fluid "F" therethrough prior to actuation of fluid delivery device 200.

Microneedle assembly 230 may be configured similar to microneedle assembly 130 (FIG. 1) and includes a proximal hub 232 and a plurality of microneedles 234 extending distally from hub 232. Microneedles 234 may define "V"-shaped, pointed distal tips 236, or may define any other suitable configuration that facilitates puncturing of the patient's epidermis and the delivery of fluids "F" into the patient's bloodstream. Microneedle assembly 230 is axially translatable between a retracted position (FIG. 5), wherein microneedle assembly 230 is fully disposed within housing 220, and an extended position (FIG. 6), wherein microneedle assembly 230 extends distally from housing 220 and through base 240 in a distal direction for penetration through a patient's skin. Microneedle assembly 230 is engaged to fluid reservoir 210 and includes a pair of opposed apertures 238 defined at opposing sides thereof in alignment with guide channels 212 of fluid reservoir 210. A protrusion 239 extends into each of apertures 238. Protrusions 239 may be resiliently movable, or, alternatively, may be resiliently deformable from within apertures 238. More specifically, protrusions 239 may be resiliently movable from a more occluding position within apertures 238, to a less occluding position, wherein protrusions are urged at least partially out of apertures 238. As will be described below, guide channels 212 of fluid reservoir 210, apertures 238, and protrusions 239 are configured to permit microneedle assembly 230, and fluid reservoir 210 engaged thereto, to translate with respect to housing 220 between the retracted position and the extended position.

Base 240, similar to base 140 (FIG. 1), is configured to fixedly engage housing 220 at a distal end thereof. An adhesive 250 may be disposed on a distal surface 244 of base 240 to adhere transdermal fluid delivery device 200 to a patient's epidermis, or skin. As in the previous embodiment, adhesive 250 must be sufficiently strong to inhibit dislodging and repositioning of transdermal fluid delivery device 200 during the use and operations thereof. In particular, the adhesive must have sufficient strength to maintain the position of transdermal fluid delivery device 200 during the transition of microneedle assembly 230 between the retracted and extended positions and during the latching and unlatching of microneedle assembly 230 in the retracted and/or the extended position. Further, a peelable cover 255 may be disposed over adhesive 250 for maintaining the integrity of adhesive 250, for protecting transdermal fluid delivery device 200 and/or for inhibiting inadvertent adhesion of transdermal fluid delivery device 200 prior to use.

Housing 220 of transdermal fluid delivery device 200 differs from housing 120 (FIG. 1) of transdermal fluid delivery device 100 (FIG. 1) in that, instead of a rotatable collar 124 (FIG. 1) configured for translating microneedle assembly 230 between the retracted position and the extended position, housing 220 includes a pair of guide posts 222 disposed at opposing sides thereof to permit microneedle assembly 230 to translate axially along longitudinal axis "X" and with respect to housing 220. More particularly, guide posts 222 of housing 220 are slidably positioned within apertures 238 of hub 232 of microneedle assembly 230 and guide channels 212 of fluid reservoir 210. Thus, as shown in FIG. 5, when microneedle assembly 230 is disposed in the retracted position within housing 220, guide posts 222 are only partially disposed through apertures 238 of microneedle assembly 230 and guide channels 212 of fluid reservoir 210. In order to move microneedle assembly 230 to the extended position, as shown in FIG. 6, microneedle assembly 230 and fluid reservoir 210 are translated distally with respect to housing 220 such that guide posts 222 are substantially disposed through apertures 238 of microneedle assembly 230 and guide channels 212 of fluid reservoir 210.

A pair of springs 224, or other biasing members (not shown) may be provided for biasing microneedle assembly 210 toward the retracted position. Thus, as shown in FIG. 5, springs 224 are disposed about guide posts 222 of housing 220 to bias guide posts 222 apart from apertures 238 and guide channels 212, thus biasing microneedle assembly 210 toward the retracted position. Guide posts 222 further define notches 226 disposed at distal ends thereof. Notches 226 are shaped complementary to protrusions 239 of microneedle assembly 230 such that, as shown in FIG. 6, upon translation of microneedle assembly 230 to the extended position, protrusions 239 are engageable within notches 226 to retain microneedle assembly 230 in the extended position, against the bias of springs 224. More particularly, during translation of microneedle assembly 230 from the retracted position to the extended position, e.g., during translation of guide posts 222 through apertures 238 and guide channels 212, protrusions 239 are urged from apertures 238 to the less occluding position to permit passage of guide posts 222 therethrough. However, upon achieving the extended position, notches 226 permit protrusions 239 to resiliently return to the more occluding position. As such, when moved to the extended position, protrusions 239 engage notches 226 to retain microneedle assembly 230 in the extended position.

In order to release microneedle assembly 230, i.e., to permit microneedle assembly 230 to return to the retracted position, microneedle assembly 230 is translated proximally with sufficient force to disengage protrusions 239 from notches 226, allowing microneedle assembly 230 to return to the retracted position under the bias of springs 224. Alternatively, protrusions 239 may be formed from a resilient material having a specific, pre-defined period of resiliency. In other words, after a pre-determined length of time, protrusions 239 may automatically disengage from notches 226, returning microneedle assembly 230 to the retracted position. Such a feature allows fluid "F" to be delivered to the patient for a pre-determined length of time, without requiring the patient to manually move microneedle assembly 230 back to the retracted position. As such, the patient need not worry about remembering elapsed treatment time and/or may apply transdermal fluid delivery device 200 during sleep, while the supply of fluids "F" is administered only during the pre-determined length of time. As can be appreciated, the pre-determined length of time may be determined by the type of fluids to be delivered, the physical characteristics of the patient and/or the specific treatment program being followed. Fluid delivery device 200 may alternatively include a pull tab (not shown), release actuator (not shown), or other release structure for selectively disengaging protrusions 239 from notches 226. Other releasable latching structures for retaining microneedle assembly 230 in the extended position and/or the retracted position are also contemplated. The use and operation of transdermal fluid delivery device 200 is otherwise similar to that described above with respect to transdermal fluid delivery device 100.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A transdermal fluid delivery device positionable on a patient's epidermis for delivering fluid into the patient's bloodstream, comprising:

a housing defining a longitudinal axis and having a proximal end and a distal end, the housing defining a passageway extending longitudinally therethrough and including a helical cam track disposed on an inner surface of the housing;

a fluid reservoir positionable within the passageway of the housing, the fluid reservoir adapted for retaining a fluid therein;

a base member positioned at the distal end of the housing; and a microneedle assembly coupled to the fluid reservoir, the microneedle assembly including a hub and a plurality of microneedles extending distally from the hub, the hub including at least one protrusion extending outwardly therefrom that is engaged within the helical cam track, each microneedle of the plurality of microneedles including a lumen defined therethrough in communication with the fluid reservoir, wherein rotation of the housing with respect to the microneedle assembly about the longitudinal axis of the housing in a first direction urges the at least one protrusion to move along the helical cam track, thereby translating the microneedle assembly longitudinally with respect to the housing from a retracted position, wherein the plurality of microneedles are disposed within the base member, to an extended position, wherein the plurality of microneedles are advanced distally to penetrate the base member and extend distally therefrom for puncturing the patient's epidermis and delivering the fluid into the patient's bloodstream, and wherein rotation of the housing with respect to the microneedle assembly about the longitudinal axis of the housing in a second, opposite direction urges the at least one protrusion to move along the helical cam track, thereby translating the microneedle assembly longitudinally with respect to the housing from the extended position to the retracted position.

2. The transdermal fluid delivery device according to claim 1, further comprising a latching mechanism for retaining the microneedle assembly in at least one of the retracted position and the extended position.

3. The transdermal fluid delivery device according to claim 1, wherein the microneedle assembly is biased toward the retracted position.

4. The transdermal fluid delivery device according to claim 1, wherein the microneedle assembly includes a first latch member and wherein the housing includes a second, complementary latch member such that, upon movement of the microneedle assembly to the extended position, the first and second latch members engage one another to retain the microneedle assembly in the extended position.

5. The transdermal fluid delivery device according to claim 4, wherein at least one of the first and second latch members defines a pre-determined latching period, the at least one latch member configured to disengage the other latch member at the end of the pre-determined latching period to return the microneedle assembly under bias back towards the retracted position.

6. The transdermal fluid delivery device according to claim 1, further comprising a skin adhesive disposed on a distal surface of the base member for adhering the base member to the patient's epidermis.

7. The transdermal fluid delivery device according to claim 6, further comprising a peelable cover disposed about the skin adhesive to inhibit adhesion prior to removal of the peelable cover.

8. The transdermal fluid delivery device according to claim 1, wherein, in the extended position, the plurality of microneedles extend distally from the base member by about 2 mm to about 3 mm.

9. The transdermal fluid delivery device according to claim 1, wherein each microneedle of the plurality of microneedles includes a pointed distal end to facilitate at least one of penetrating the base member and puncturing the patient's epidermis.

* * * * *